US006423002B1

(12) United States Patent
Hossack

(10) Patent No.: US 6,423,002 B1
(45) Date of Patent: Jul. 23, 2002

(54) INTRA-OPERATIVE DIAGNOSTIC ULTRASOUND MULTIPLE-ARRAY TRANSDUCER PROBE AND OPTIONAL SURGICAL TOOL

(75) Inventor: John A. Hossack, Palo Alto, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/339,923

(22) Filed: Jun. 24, 1999

(51) Int. Cl.$^7$ ................................................ A61B 8/00
(52) U.S. Cl. ........................................ 600/439; 128/916
(58) Field of Search ................................. 600/437, 439, 600/443, 447, 458–459, 463, 461, 471

(56) References Cited

U.S. PATENT DOCUMENTS

| | | | |
|---|---|---|---|
| 3,888,238 A | 6/1975 | Meindl et al. ............... 128/2 V |
| 4,681,103 A | 7/1987 | Boner et al. ............. 128/303 B |
| 4,868,476 A | * 9/1989 | Respaut ..................... 73/618 X |
| 5,013,312 A | 5/1991 | Parins et al. .................... 606/37 |
| 5,201,731 A | 4/1993 | Hakky .......................... 606/15 |
| 5,335,663 A | * 8/1994 | Oakley et al. ............... 600/463 |
| 5,368,037 A | 11/1994 | Eberle et al. .......... 128/662.06 |
| 5,415,175 A | 5/1995 | Hanafy et al. ......... 128/662.03 |
| 5,471,988 A | 12/1995 | Fujio et al. ............ 128/660.03 |
| 5,487,386 A | * 1/1996 | Wakabayaski et al. ...... 600/437 |
| 5,608,690 A | 3/1997 | Hossack et al. ............. 367/138 |
| 5,680,863 A | 10/1997 | Hossack et al. ........ 128/662.03 |
| 5,704,361 A | * 1/1998 | Seward et al. ............... 128/916 |
| 5,776,067 A | * 7/1998 | Kamoda et al. ............. 128/916 |
| 5,799,661 A | 9/1998 | Boyd et al. .................. 128/898 |
| 5,846,205 A | 12/1998 | Curley et al. ................ 600/472 |
| 5,873,830 A | * 2/1999 | Hossach et al. ............. 600/447 |
| 5,876,345 A | 3/1999 | Eaton et al. ................. 600/466 |
| 5,891,039 A | 4/1999 | Bonnefous et al. ......... 600/454 |
| 6,066,096 A | * 5/2000 | Smith et al. ................. 600/439 |

* cited by examiner

*Primary Examiner*—Francis J. Jaworski
(74) *Attorney, Agent, or Firm*—Brinks Hofer Gilson & Lione

(57) ABSTRACT

A system, method and probe for diagnostic ultrasound imaging with at least two, and preferably three transducer arrays. The first transducer array provides a primary image. The second transducer array comprises an array of transducer elements positioned near one end of the first transducer array for providing an image in a different plane. An optional third transducer array comprises an array of transducer elements positioned near the other end of the first transducer array for providing an additional image in a different plane. One application of the invention is to collect tissue for medical procedures, wherein at least one surgical tool is attached to the probe near the imaging arrays and moves together with at least one imaging array. As the primary imaging array is drawn across tissue for collection, the operator observes a cross-section of the tissue prior to actually cutting the tissue. Another application of the invention allows an operator to selectively display pseudo 3-D images or 3-D images, using the same probe. Another application of the invention allows an operator to determine the 3-D position of a foreign object in body tissue.

67 Claims, 6 Drawing Sheets

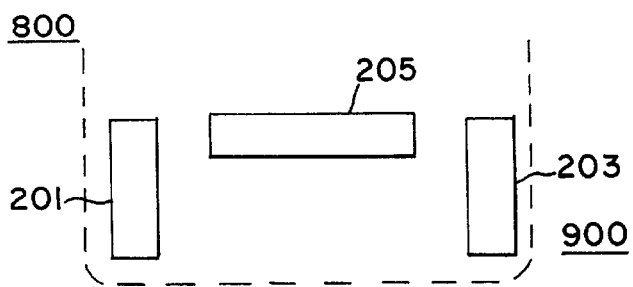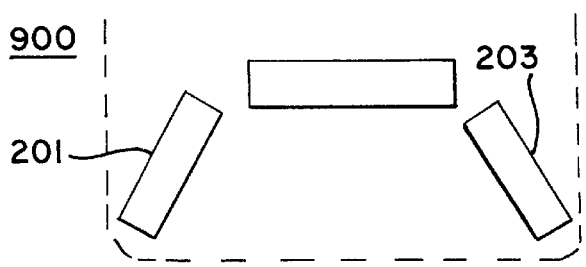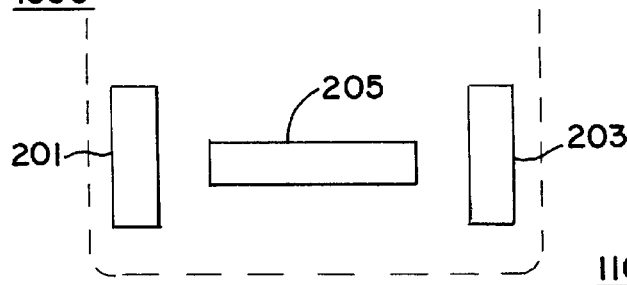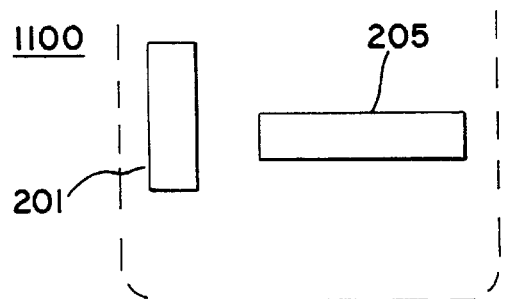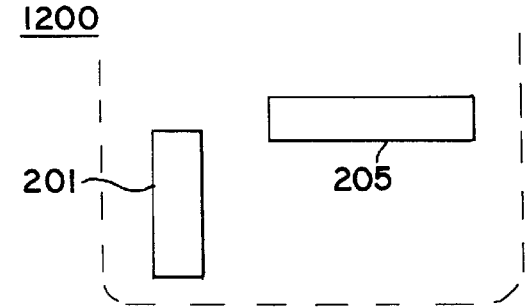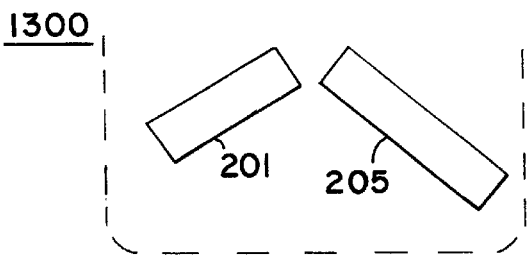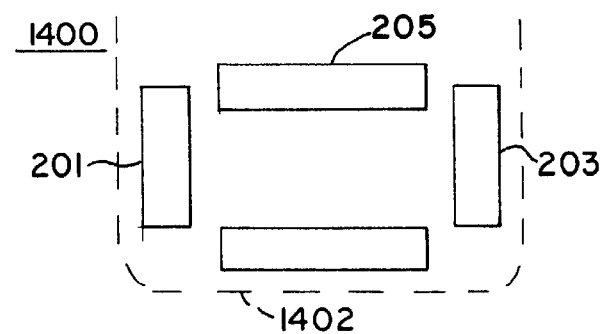

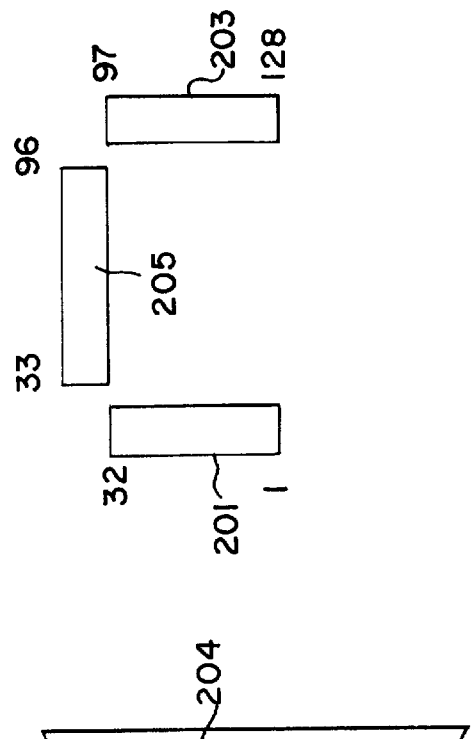
FIG.16(a)
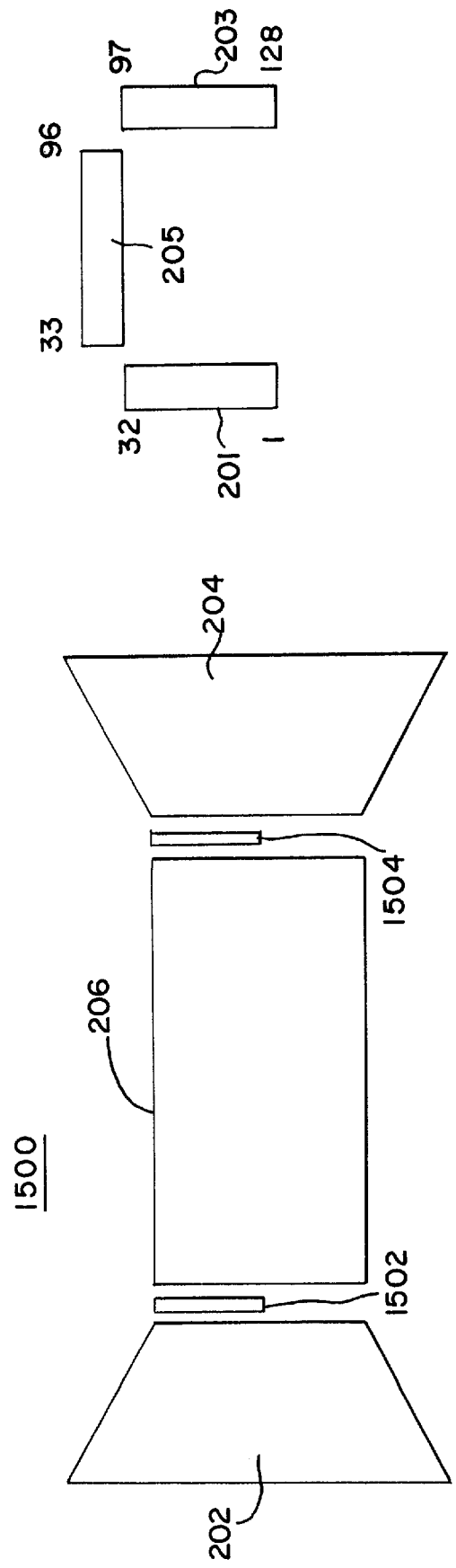
FIG.15
FIG.16(b)
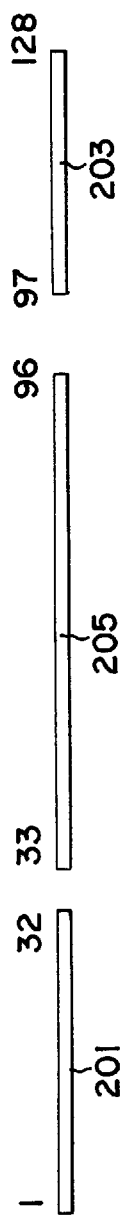

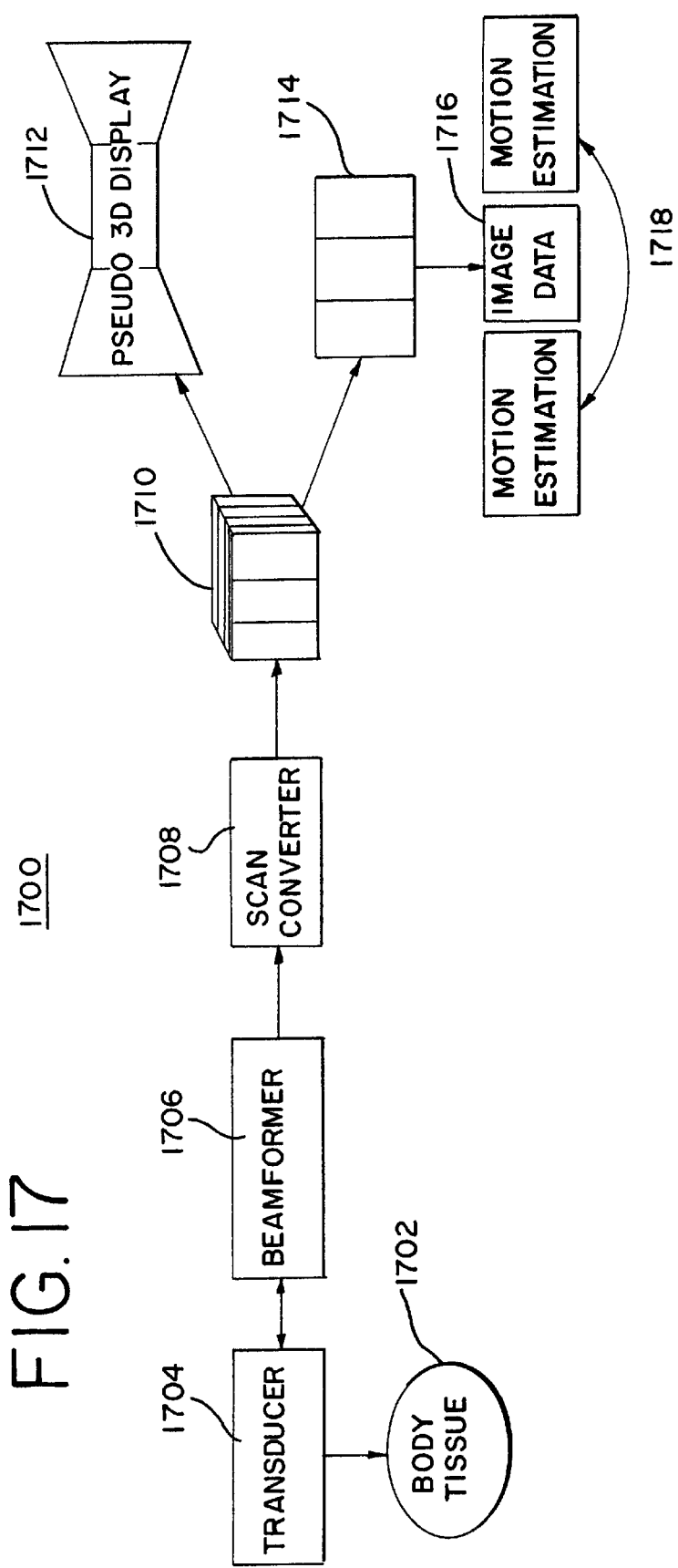

INTRA-OPERATIVE DIAGNOSTIC ULTRASOUND MULTIPLE-ARRAY TRANSDUCER PROBE AND OPTIONAL SURGICAL TOOL

BACKGROUND OF THE INVENTION

1. Field of Invention

This invention relates to an improved system, method, and probe for acquiring two-dimensional (2-D) diagnostic ultrasound image information and associated relative positional information to allow subsequent three-dimensional (3-D) or pseudo 3-D imaging for tissue assessment and collection.

2. Description of the Prior Art

There is growing interest in 3-D ultrasound images for medical applications. The commonly available ultrasound systems for medical applications normally provide one-dimensional (1-D) ultrasound transducer arrays or 2-D ultrasound transducer arrays for obtaining images. One approach is to use a 2-D ultrasound transducer array to obtain 3-D image information directly. A 2-D ultrasound transducer array can be used to scan electronically in any desired orientation, and thereby acquire the desired information.

The prior art for surgical application of probes with ultrasound imaging transducers has been directed at very specialized applications, such as catheters for imaging blood flow inside blood vessels or arterial blockage. These catheters sometimes include a biopsy needle or the equivalent for taking samples of material found inside a blood vessel. But there is no disclosure of tissue collecting tools with 3-D ultrasound imaging for operation outside of blood vessels.

What is needed is an improved system, method, and probe to obtain 3-D or pseudo 3-D images of difficult-to-image body tissues during collection. The improved system, method, and probe should be relatively low cost and permit examination and efficient collection of arteries and other tissues for re-use in surgical procedures.

SUMMARY OF THE INVENTION

One object of the present invention is to provide a system, method, and probe to obtain 3-D or pseudo 3-D images of body tissues during collection that are difficult to assess with rotated 2-D images. Primary and secondary imaging information need to be provided concurrently, such that the secondary imaging information can be used to estimate the movement of the transducer probe and/or the body tissue between respective image data frames.

Another object of the invention is to provide a relatively low cost system, method, and probe to permit examination and efficient collection of tissues for re-use in surgical procedures.

Another object of the invention is to allow an operator to determine the position of a foreign object in body tissue with a multiple array ultrasound imaging probe.

A first aspect of the invention is directed to an intra-operative ultrasound probe that includes a support element and a first and a second imaging transducer array coupled to move with the support element. The first transducer array provides a primary imaging array image plane, and includes an array of transducer elements arranged along the azimuthal axis, with first and second ends spaced along the azimuthal axis. The second transducer array includes an array of transducer elements positioned near the first end of the first transducer array to provide a secondary imaging array plane non-parallel to the primary imaging array image plane. A therapeutic tool is attached adjacent to one of the transducer arrays, and moves together with the transducer arrays.

A second aspect of the invention is directed to imaging in non-parallel first and second image planes and simultaneously displaying the first image and the distorted second image to produce a pseudo 3-D image.

A third aspect of the invention is directed to a medical ultrasound imaging system which allows an operator to select between pseudo 3-D imaging and 3-D imaging with a multiple array ultrasound imaging probe and display the pseudo 3-D images or the 3-D images. The multiple array imaging probe includes a principal array used for imaging, and a secondary array which can selectively function as an imaging array to provide imaging data for pseudo 3-D imaging, or function as a tracking array to provide motion estimation data regarding the principal array for 3-D imaging.

A fourth aspect of the invention is directed to allowing an operator to determine the position of a foreign object in body tissue with an ultrasound imaging probe having a first transducer array and a second transducer array. The first transducer array is swept across the body tissue to provide multiple images and the second transducer array provides motion estimates to construct 3-D images of the body tissue and the foreign object. 3-D images of the body tissue and the foreign object are then displayed.

These and other objects and advantages of the invention will become apparent to those skilled in the art from the following detailed description of the invention and the accompanying drawings.

BRIEF DESCRIPTION OF THE DRAWINGS

FIG. 8 is a schematic top view of a transducer probe with a basic three array configuration.

FIG. 9 is a schematic top view of a transducer probe with another three array configuration.

FIG. 10 is a schematic top view of a transducer probe with a symmetric three array configuration.

FIG. 11 is a schematic top view of a transducer probe with one type of two array configuration.

FIG. 12 is a schematic top view of a transducer probe with a second type of two array configuration.

FIG. 13 is a schematic top view of a transducer probe with a two array chevron configuration.

FIG. 14 is a schematic top view of a transducer probe with a four array configuration.

FIG. 15 is a perspective view of a display image with a tool depth icon.

FIG. 16(a) shows an example of an ultrasound system with 128 channels allocated to the 128 elements of a 64 element primary imaging array and two 32 element secondary imaging arrays.

FIG. 16(b) shows how the ultrasound system can consider a primary imaging array and two secondary imaging arrays as acting as one linear array of 128 elements.

FIG. 17 shows how the ultrasound system can interpret the data obtained from a multiple array probe and construct a pseudo 3-D display or a 3-D display, where the secondary array is used as a tracking array providing motion estimation data.

DETAILED DESCRIPTION OF PREFERRED EMBODIMENTS OF THE INVENTION

Figure 1:
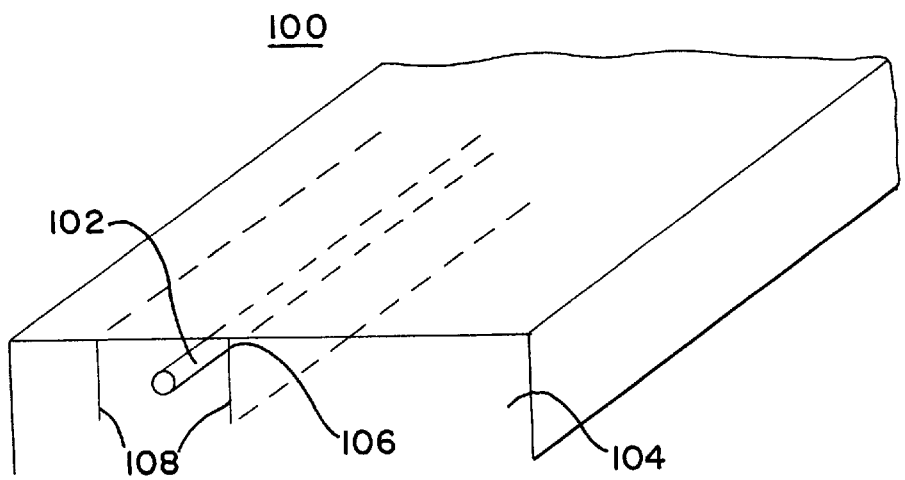
FIG. 1 is a perspective view of tissue surgery on a human body wall.

The invention provides an intra-operative ultrasound probe for tissue examination and collection of tissue to be used for surgical procedures. In one preferred embodiment of the invention, the probe includes two imaging transducer arrays, and a therapeutic tool that moves together with the imaging transducer arrays. One imaging transducer array provides a primary image, and another imaging transducer array acts as a secondary imaging array to provide a side image of an object shown on the primary image. Preferably, the intraoperative ultrasound probe provides imaging in two non-parallel image planes, and simultaneously displays the two image planes with a geometric transformation to produce a pseudo 3-D image.

The invention is typically implemented with miniature, phased ultrasound arrays placed on the end of a suitable probe shaft. The ultrasound primary and secondary imaging arrays need not be the same, but the system configuration is simplified if they are the same.

In a typical embodiment, the ultrasound primary imaging array comprises 64 to 96 elements in a line, with a 12 Megahertz (MHz) center frequency on a 0.1 to 0.2 millimeters (mm) element-to-element pitch. The elements are typically between 2 and 4 mm in elevation dimension (i.e., perpendicular to the array or azimuthal axis). The ultrasound secondary imaging arrays typically comprise 16 to 32 elements, each side array having the same center frequency, pitch, and elevation dimension as the primary imaging array. In one preferred embodiment of the invention the transducer has a primary array having 64 elements with a 12 MHz center frequency on a 0.1 mm element-to-element pitch, and a 2 mm elevation dimension, and two secondary imaging arrays, each with 32 elements with the same frequency, pitch, and elevation dimension as the primary array. The scan format of the arrays may be of any type (e.g., linear, sector, Vector® wide view, curvilinear, curved Vector® wide view, or radial).

In a preferred embodiment, the entire probe diameter is 5 to 12 mm. For initial invasive surgery, the entire probe diameter is less than 10 mm and the length of the probe is between 15 to 30 centimeters (cm).

Typically, the support for the arrays is either a rigid plastic handle 15 to 30 cm long, or a flexible handle optionally including user-controllable articulation. Preferably, if user-controllable articulation is provided, it is similar to the 2-way or 4-way articulation provided in transesophageal (TEE) probes known in the prior art. For example, articulated probes are commercially available from Instrument Technology, Inc., located in Westfield, Mass.

An alternative embodiment of the invention has a handle with a semi-rigid user-formable core. One example of this embodiment is a spiral indented, thin-walled copper tube (similar to a small scale flexible water plumbing pipe) which is formed by a surgeon to the desired shape. The copper tube maintains the desired shape while the surgeon probes with the invention through a body opening.

One surgical application for the invention is tissue imaging for the inefficient collection of distinct types of tissues, particularly arteries, to assist in the process of forming a satisfactory graft. FIG. 1 is a perspective view 100 of artery 102 surgery on a human body wall 104. A branch-off artery 106 and the desired pair of parallel cuts 108 are also shown.

Figure 2:
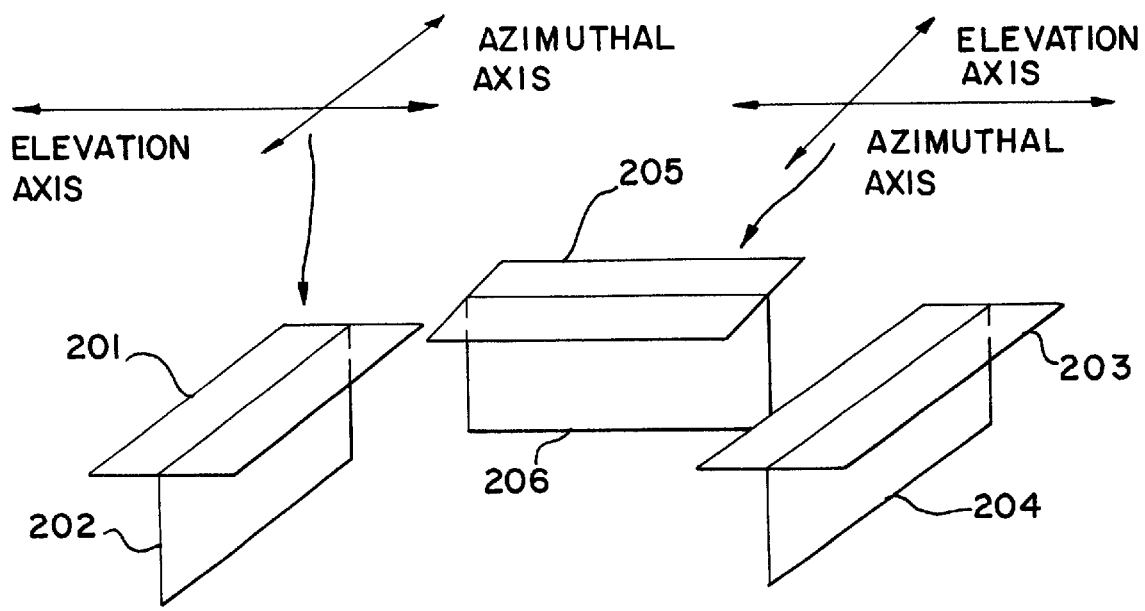
FIG. 2 is a perspective view of a transducer configuration with two secondary imaging arrays, and a primary imaging array.

FIG. 2 is a perspective view of a transducer configuration 200 with two secondary imaging array image planes 202 and 204, and primary imaging array image plane 206, corresponding, respectively, to secondary imaging arrays 201 and 203, and primary imaging array 205. In the preferred embodiment of the invention, different images are acquired with the different transducer arrays. The different transducer arrays are configured such that the azimuthal axes of secondary imaging arrays 201 and 203 are non-parallel to the azimuthal axis of primary imaging array 205. In one preferred embodiment of the invention, the azimuthal axes of secondary imaging arrays 201 and 203 are perpendicular to the azimuthal axis of primary imaging array 205. The azimuthal and elevation axes are also shown for primary imaging array 205 and secondary imaging array 201, illustrating the relationship of these axes to an array.

Figure 3:
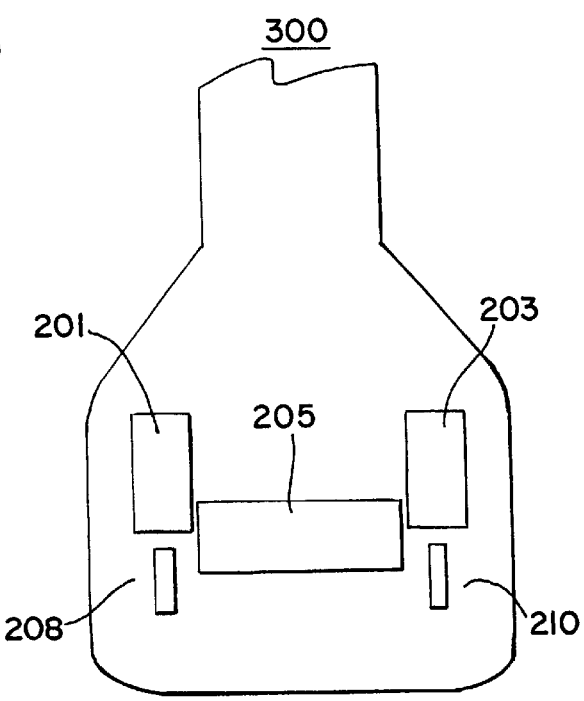
FIG. 3 is a schematic top view of the transducer probe.

FIG. 3 is a schematic top view of a transducer probe 300. It shows two secondary imaging arrays 201 and 203, primary imaging array 205, and two optional surgical blades 208 and 210. In one preferred embodiment of the invention, one or more surgical tools move together with the arrays, and are attached to the tip of the probe near secondary imaging arrays 201 and 203. In an alternative preferred embodiment, two surgical cutting tools move together with the arrays, and are distally placed from secondary imaging arrays 201 and 203. The cutting tools are either surgical steel blades, or alternatively, are based on electrocautery principles (tissue-burning). Preferably, the cutting tools are attached to the same support element that supports secondary imaging arrays 201 and 203, and primary imaging array 205. As primary imaging array 205 is drawn across tissue containing a desired structure (e.g., an artery for collection), the surgeon observes the cross-section of the desired structure (e.g., the artery) in imaging array plane 206 (not shown) of primary imaging array 205.

Figure 4:
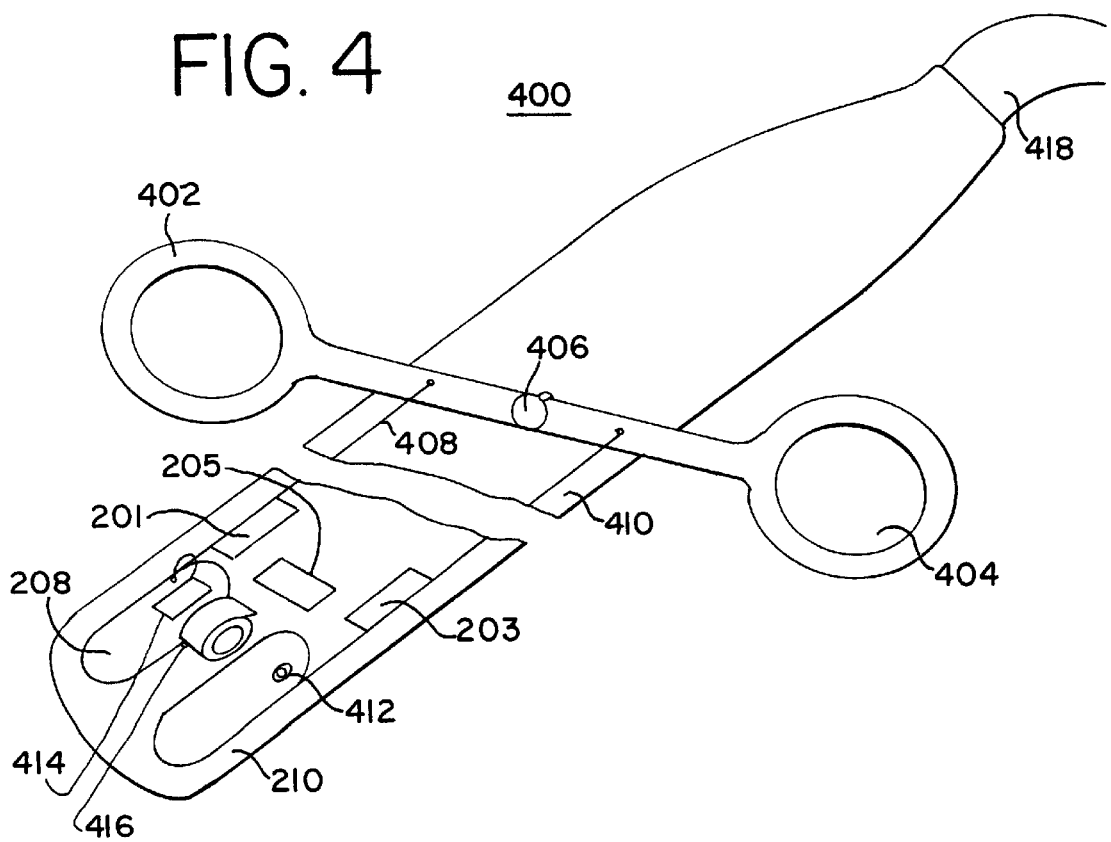
FIG. 4 is a perspective view of the transducer's secondary imaging arrays, primary imaging array and retractable blade system.

FIG. 4 is a perspective view of one preferred configuration 400 of secondary imaging arrays 201 and 203, primary imaging array 205, and a retractable blade system. The retractable blade system is comprised of two surgical blades 208 and 210, which are user-controlled by finger hoops 402 and 404, and mounted on first pivot 406. Surgical blades 208 and 210 are activated or retracted by the relative amount of tension exerted on control wires 408 and 410, as exerted by a surgeon pulling on finger hoops 402 and 404. Preferably, the attachment point for control wires 408 and 410 would be close to first pivot 406 for increased mechanical leverage when the surgeon pulls on finger hoops 402 and 404. Surgical blades 208 and 210 are mounted on second pivot 412, and are normally retracted by springs 414 and 416 into non-cutting positions. In one embodiment of the invention, springs 414 and 416 are small coil springs, such as found in a clock. A strain gauge (not shown) is optionally attached to springs 414 and 416 to monitor the deployment of surgical blades 208 and 210. System cable 418 electronically connects the invention to the remainder of the ultrasound imaging system (not shown).

Figure 5:
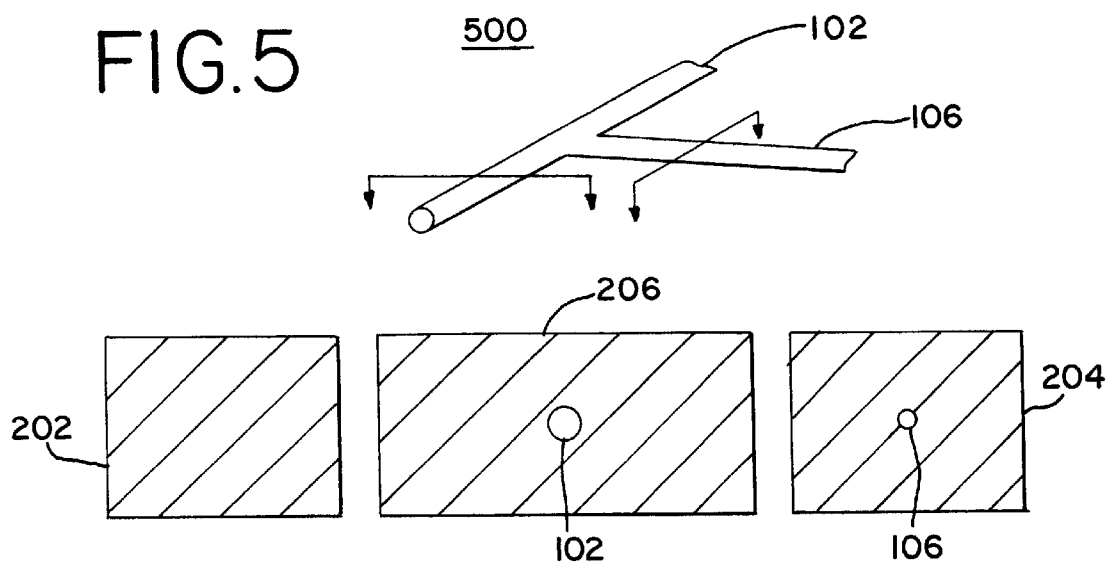
FIG. 5 is a perspective view of a portion of an artery and the corresponding image shown by the primary and secondary imaging arrays.

FIG. 5 is a perspective view of a portion of artery 500, including artery 102 and branch-off artery 106. This perspective view includes corresponding images of these arteries in secondary imaging array image planes 202 and 204, and primary imaging array image plane 206, with cross-section views of artery 102 and branch-off artery 106 taken along the lines shown.

Figure 6:
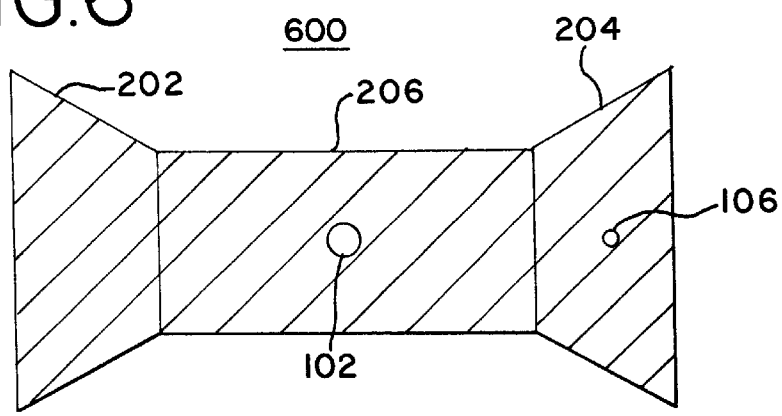
FIG. 6 is a perspective view of the preferred display with perspective correction.

FIG. 6 is a perspective view of one preferred display 600 with perspective correction, showing how artery 102 and branch-off artery 106 would appear in corresponding images shown in secondary imaging array image planes 202 and 204, and primary imaging array image plane 206.

Figure 7:
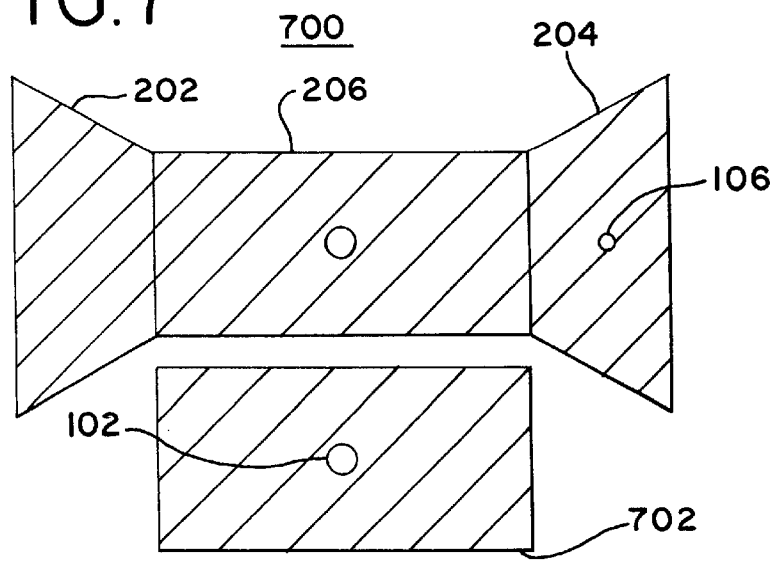
FIG. 7 is a perspective view of a second preferred display with perspective correction and a shadow image.

FIG. 7 is a perspective view of a second preferred display 700 with perspective correction and shadow image plane 702, showing how artery 102 and branch-off artery 106 would appear in corresponding images shown in secondary imaging array image planes 202 and 204, and primary imaging array image plane 206. Shadow image plane 702 can be presented as a translucent, highlighted, or de-emphasized image, depending on the application of the intraoperative ultrasound probe. Shadow image plane 702 is provided by second primary imaging array 1402 (shown in FIG. 14) and may be superimposed next to primary imaging array image plane 206 so that a surgeon has an advance view of a cross-section of the desired tissue, well before actually cutting the desired tissue. Additionally, the two secondary imaging array image planes 202 and 204 can show the tissue immediately up-stream from the surgical cutting tools before cuts are made. In this manner, a surgeon can keep the cutting tools aligned with the center of the desired tissue (e.g., a section of the artery), and receive advance warning of any complications in the cutting path before the cuts are made. An example of a complication is the presence of one or more branch-off arteries from the desired artery. These branch-off arteries require the surgeon to slow down or change his procedure, so that the surgeon can correctly collect the artery and block the ends of the branch-off arteries to prevent blood leakage.

Optionally, a surgical tool is placed so that it is visible at one extreme of the secondary imaging array image. In a preferred embodiment of the invention, the surgical tool is user-controllable (e.g., retractable). Therefore, the surgeon can make a dry run through the procedure without cutting tissue. In a preferred embodiment of the invention, a surgeon scans the region surrounding the blood vessel of interest using a 3-D representation of the region. One preferred 3-D representation uses the invention described in co-pending U.S. patent application Ser. No. 08/916,585, filed on Aug. 22, 1997, entitled "Multiple Ultrasound Image Registration System, Method and Transducer," which is assigned to the assignee of the present invention and hereby incorporated by reference.

FIG. 8 is a schematic top view of a transducer probe with a basic three array configuration 800. It shows two secondary imaging arrays 201 and 203, and primary imaging array 205. But there are alternative embodiments of a three array configuration with different relative placements of secondary imaging arrays 201 and 203, and primary imaging array 205. For example, the primary imaging array 205 could be shifted relative to secondary imaging arrays 201 and 203.

FIG. 9 is a schematic top view of a transducer probe with another three array configuration 900. It shows two secondary imaging arrays 201 and 203, and primary imaging array 205, where the azimuthal axes of secondary imaging array 201 and 203 are non-orthogonal, but still non-parallel, to the azimuthal axis of primary imaging array 205.

FIG. 10 is a schematic top view of a transducer probe with a symmetric three array configuration 1000. It shows primary imaging array 205 symmetrically centered in between two secondary imaging arrays 201 and 203. In an alternative embodiment of the invention, the azimuthal axes of secondary imaging array 201 and 203 are non-orthogonal, but still non-parallel, to the azimuthal axis of primary imaging array 205.

FIG. 11 is a schematic top view of a transducer probe with a two array configuration 1100. It shows one secondary imaging array 201 and one primary imaging array 205 where primary imaging array 205 is centered orthogonally to secondary imaging array 201, and primary imaging array 205 is at one end of secondary imaging array 201. In an alternative embodiment of the invention, the azimuthal axis of secondary imaging array 201 is non-orthogonal, but still non-parallel, to the azimuthal axis of primary imaging array 205. In a preferred alternative embodiment of the invention, this asymmetric configuration with one primary imaging array 205 and one secondary imaging array 201 includes one or more cutting tools (not shown) near secondary imaging array 201. The cutting tool or tools may be distally or proximally placed to secondary imaging array 201, depending on whether the desired cutting direction is advancing forward into the body or retracting outwards from the body.

FIG. 12 is a schematic top view of a transducer probe with a second type of two array configuration 1200. It shows one secondary imaging array 201 and one primary imaging array 205 where primary imaging array 205 is orthogonal to secondary imaging array 201, and primary imaging array 205 is at one end of secondary imaging array 201.

FIG. 13 is a schematic top view of a transducer probe with a two array chevron configuration 1300. It shows one secondary imaging array 201 and one primary imaging array 205 where primary imaging array 205 is non-parallel to secondary imaging array 201, and primary imaging array 205 and secondary imaging array 201 form a symmetrical chevron. In this case, primary imaging array 205 and secondary imaging array 201 would typically be identical.

FIG. 14 is a schematic top view of an ultrasound transducer probe with a four array configuration 1400. It shows secondary imaging arrays 201 and 203, and primary imaging array 205 and second primary imaging array 1402. This embodiment of the invention has the fourth array (second primary imaging array 1402) placed parallel to first primary imaging array 205 to form a full square of arrays around the region of interest. A transparent, or edge detected, shadow image plane 702 (shown in FIG. 7) from this second primary imaging array 1402 may be superimposed next to the image plane 206 (shown in FIG. 7) from primary imaging array 205 so that a surgeon has an advance view of a cross-section of the desired tissue, well before actually cutting the desired tissue.

Pseudo 3-D Display

A preferred embodiment of the invention with three transducer arrays, when used with an ultrasound system (e.g., an Acuson Sequoia® ultrasound system or an Aspen™ ultrasound system), will produce a three segment image. The three segment image will display the image data plane from the primary imaging array in the center, between the secondary image data planes from the two secondary imaging arrays.

A low cost, esthetically pleasing segmented display image is obtained by distorting the secondary image data planes from a rectangular format (for a is linear format) to a trapezoidal format, such that the secondary imaging array data plane image lines are made to appear shorter and hence further away. For example, this is achieved by using a simple pixel transform mapping operation in the scan-converter.

Alternatively, this can be accomplished by post-processing after scan conversion and before display. This gives the perception of a 3-D perspective view, where the primary imaging array data plane is the central imaging plane next to one or two secondary imaging array data planes. This is referred to as a pseudo 3-D display. In an alternative embodiment, the primary imaging array data plane is arranged to look bigger and hence closer, if this visual orientation is preferred. FIG. 13 shows a two array, symmetrical arrangement, where primary imaging array 205 forms a chevron with secondary imaging array 201. Distortion could be applied to secondary imaging array image plane 202 (not shown) and primary imaging array image plane 206 (not shown) to make the region closer to the viewer look bigger and the region farther from the viewer look smaller, or vice versa.

FIG. 15 is a perspective view of a display image 1500 with tool depth icons 502 and 1504 in relation to secondary imaging array image planes 202 and 204, and primary imaging array image plane 206. One or more surgical tools move together with the arrays and are preferably attached to the same support element supporting the arrays. Examples of surgical tools that can be used with the invention are: surgical blades, electrocautery knives, a high power laser, and a radio-frequency (RF) ablation device. Any other tool for cutting, burning, freezing, or otherwise removing or destroying tissue may be used with the invention. These tools may also be retractable. Preferably, if the cutting tool is retractable, the degree of deployment is monitored by a motion transducer, for example, by a strain gauge attached to a position retaining spring. This feedback of deployment depth is communicated to the ultrasound imaging system, and the motion transducer value is converted to a depth value via a look-up table. Once the ultrasound imaging system has tool depth information, an alphanumeric display or suitable graphic tool depth icons 1502 and 1504 are placed on the ultrasound display image 1500 to indicate current cutting depth. Alternatively, the depth information can be conveyed to the user by an audible tone (e.g., by a tone that increases in volume or pitch as cutting depth increases). This information enables a surgeon to decide whether to further extend or retract the cutting tool. In one embodiment of the invention, the cutting tool is activated (i.e., blade extended) by pulling finger hoops 402 and 404, as is shown in FIG. 4. In a simpler embodiment, the cutting tool can have just two states: retracted and extended. Again, these states can be displayed to the surgeon either visually, audibly, or both.

FIG. 16(*a*) shows an example of an ultrasound system with 128 channels allocated to the 128 elements of 64 element primary imaging array 205 and two 32 element secondary imaging arrays 201 and 203. FIG. 16(*b*) shows how the ultrasound system can consider primary imaging array 205 and secondary imaging arrays 201 and 203 as acting as one linear array of 128 elements. This ultrasound system treatment of all the elements of all the arrays as elements in one large, linear array can create array cross-talk interference, if transmitted or received pulses involve more than one array.

A preferred embodiment of the invention includes transmit and receive beamforming apertures, with permanent aperture limits incorporated at the array boundaries to eliminate array cross-talk interference. These permanent aperture limits are preferably implemented in software and maintain the functional identity of each transducer array.

One potential application for the invention, as discussed above, is for surgery on arteries. The invention can be used in either a minimally invasive procedure or in a conventional sternotomy (open chest) procedure, and is particularly useful in imaging obese persons whose arteries can be difficult to see. Furthermore, in the minimally invasive environment, a surgeon cannot use his fingers to feel for arterial pulsing during surgery and must be aware of the nearby associated veins. The surgeon must also be aware of nearby nerves and nerve branches. The ability to see these features is a significant advantage for achieving fast and effective surgery. Conventionally, and almost always in a minimally invasive procedure, a section of tissue is taken around the artery, leaving a tissue margin of approximately 5 to 10 mm around the artery. This protects the artery and minimizes the danger of damage to the artery. With the present invention, the surgeon sees a cross-section of the artery and the perpendicular cut planes immediately in advance of and coplanar with the cutting blades. In one embodiment of the invention, these blades are independently controllable by means of finger loops. Additional retaining springs (for example, small clock springs) serve to return the blades to the safe retracted position when no finger pressure is applied. Once parallel cuts are made on either side of the artery, it is gently spooned out using a blunt blade (e.g., an inactive cautery tool). The surgical procedure continues in a conventional manner, except that an imaging transducer array is optionally used to visualize artery performance prior to grafting.

Another application is for scanning organs for perfusion (i.e., fluid flow through lumens in the organs). Since the perfusion measurement requires a very high quality of image in terms of spatial and contrast resolution, it is preferable to use a high frequency ultrasound primary imaging array in intimate contact with the organ. Preferably, the primary imaging array can operate in the 10 to 20 MHz center frequency range. The secondary imaging arrays can provide data for making a 3-D image, or data for quantitative measurements of the dimensions of the region of interest in the elevation direction of the primary imaging array.

Another application of the invention is scanning the heart muscle directly for evidence of infarct or lack of perfusion. Since a probe according to the invention uses multiple array imaging, using an estimate of relative motion as described in co-pending U.S. patent application Ser. No. 08/916,585, it is feasible to make a 3-D scan even if the organ is in motion. However, there will be some distortion due to the fact that the organ may be contracting or expanding, as well as simply shifting under the probe. The heart rate is typically slowed down during operation, thus making scanning simpler. If the organ motion reverses during the scan, there may be duplicate data acquired. This duplicate data can be used during the 3-D reconstruction, or it may be removed and only non-redundant data used in the reconstruction.

In carrying out the invention, any type of ultrasound data can be used, alone or in combination. Specifically, any of the following ultrasound imaging modalities can be used in accordance with the embodiments taught herein, with either fundamental or harmonic imaging or a combination thereof, either in the presence or in the absence of contrast agent: B-mode, Color Doppler Velocity, Color Doppler Energy, Color Doppler Variance, Doppler Tissue Velocity, Doppler Tissue Energy, Doppler Tissue Acceleration or any combination thereof. One preferred embodiment of the invention uses Doppler imaging as disclosed in co-pending U.S. patent application Ser. No. 08/736,895, filed Oct. 25, 1996, entitled "Imaging Modality Showing Energy and Velocity," which is assigned to the assignee of the present invention and hereby incorporated by reference.

Doppler velocity imaging allows a surgeon or sonographer to identify with confidence an artery by its pulsatile (i.e., throbbing or beating) characteristic. The surgeon can also monitor the blood flow in the coronary arteries by directly placing the probe on the heart surface (or through the pericardium, if it is intact). In this way, the surgeon can monitor the presence of a blockage and verify the positioning of a graft. This is superior to the prior art method involving manually correlating what is observed during the operation with an earlier angiogram. Such an angiogram, taken when the patient was possibly lying in a different orientation, could result in a mistake in placing a graft. When Doppler imaging is a primary interest, it is preferable to design the primary imaging array to form less than a 90 degree angle to the vessel of interest, so that a better Doppler signal is obtained.

3-D Imaging and Pseudo 3-D Imaging

The various multiple array ultrasound probes described herein can alternatively be used for 3-D imaging as described in co-pending U.S. patent application Ser. No. 08/916,585. Secondary imaging arrays that are used for pseudo 3-D imaging in an intra-operative ultrasound probe could function as tracking arrays for 3-D ultrasound image construction from a series of successive image planes obtained from sweeping a principal transducer array along the elevation axis (see FIG. 2). Typically, these pseudo 3-D imaging and 3-D imaging capabilities would be implemented by incorporating software routines for pseudo 3-D and 3-D imaging. Hence, it would be desirable for an ultrasound system to provide the capability for a surgeon or sonographer to easily switch the function of the secondary transducer array(s) from providing images for pseudo 3-D imaging to tracking the motion of the principal transducer array. The ultrasound system could allow the surgeon or sonographer to select pseudo 3-D imaging or 3-D imaging by voice command, keyboard, foot pedal, or graphical user interface (e.g., mouse, trackball, touchpad, or other equivalent operator interfaces).

FIG. 17 shows how the ultrasound system can interpret the data obtained from a multiple array probe and construct a pseudo 3-D display or a 3-D display, wherein a secondary array is used as a tracking array to provide motion estimation data as the principal transducer array is swept in the elevation direction. Body tissue 1702 is imaged by transducer 1704 transmitting pulses generated by beamformer 1706. Beamformer 1706 also receives signals from transducer 1704 which are converted and presented to scan converter 1708 to produce data sets 1710. Data sets 1710 can be displayed as pseudo 3-D data 1712 or interpreted as 3-D data 1714, which is separated into image data 1716 and motion estimation data 1718 for 3-D image construction.

A multiple array ultrasound probe capable of providing a 3-D display and/or a pseudo 3-D display described above could also be used to determine the position of a foreign object in body tissue. Such foreign objects include surgical tools, catheters, e.g., intra-vascular ultrasound (IVUS) catheters, gallstones, bullets, pellets, shrapnel, and other projectile material.

One preferred embodiment of the invention uses a multiple array ultrasound probe in combination with an WUS catheter. During an operation, an IVUS catheter can monitor conditions of an organ accurately, while a multiple array ultrasound probe unambiguously identifies the location of the IVUS catheter. For example, the IVUS catheter may be within a heart's coronary artery, while the intra-operative 3-D ultrasound probe scans the external surface of the heart muscle and identifies the location of the IVUS catheter with respect to the external surface of the heart.

Piano-concave type arrays, e.g., as described in U.S. Pat. No. 5,415,175 to Hanafy et al., or 1.5-D type arrays (comprising a small number of element segments along the elevation direction of the array) can also be used as primary imaging arrays or secondary imaging arrays if required. Such arrays provide the capability of simulating a wider aperture 2-D ultrasound transducer array. Other types of arrays could also be used, e.g., annular arrays, linear, non-phased arrays, radial arrays or sector arrays, as described in U.S. Pat. No. 5,876,345 to Eaton et al.

Optionally, the invention is incorporated in disposable or reusable ultrasound imaging probes. If the ultrasound imaging probe is disposable, a low melting point plastic is used (e.g., soft Pebax®) so that is unambiguously damaged by re-sterilization efforts. In the most preferred embodiment of the invention, the plastic material is Pebax® polyether block amide, available from Elf Atochem North America, located in Philadelphia, Pa. If the ultrasound imaging probe is reusable, a plastic sheath is used which is tolerant of at least one application of chemical sterilization, steam sterilization (autoclaving), or Steris sterilization. Plastics that can be used for these embodiments include: Pellethane® thermoplastic polyurethane elastomer available from Dow Corporation, located in Midland, Mich., and Hytrel® polyester elastomer, available from Du Pont Corporation, located in Wilmington, Del.

In a preferred embodiment of the invention, a limited use control method, such as assigning a unique identification number (e.g., by means of electrically programmable fuses) to each ultrasound imaging probe, is used in combination with the sterilization. Software is used to monitor and check the number of times that the ultrasound imaging probe has already been used. The apparatus and method for limited use control of a probe are more fully described in a co-pending U.S. patent application filed on the same day as this application, entitled "Apparatus and Method to Limit the Life Span of an Ultrasound Probe," which is assigned to the assignee of the present invention and hereby incorporated by reference. Additionally, all variations for processing and operation described in co-pending U.S. patent application Ser. No. 08/916,585 can be applied to the invention and are incorporated by reference.

The exemplary embodiments described herein are for purposes of illustration and are not intended to be limiting. Examples of variations within the scope of this invention include, but are not limited to, the following:

The geometric distortion of the secondary imaging array planes can be performed pre-scan conversion, rather than be performed during or post-scan conversion.

Different distortion algorithms can be implemented for presenting the secondary imaging array planes.

The probe described herein can provide pseudo 3-D imaging without cutting tools.

The probe can have one cutting tool to make one cut at a time.

The probe spacing between the cutting tool or tools relative to the ultrasound transducer arrays can be altered according to need.

The probe can implement different retracting mechanisms for the cutting tool or tools.

Sub-apertures of a 2-D transducer array can provide two or more imaging arrays.

One or more cutting tools can be represented by icons, symbols, alphanumeric characters, or graphical displays.

The selection of a 3-D imaging mode or pseudo 3-D imaging mode by an operator would not preclude provision of a default imaging mode assumed by the medical ultrasound system. 3-D images and pseudo 3-D images could be displayed simultaneously on one display device or on separate display devices.

A multiple array ultrasound imaging probe can allow determination of the position of a foreign object in body tissue, and the information conveyed on a display could include icons, numeric or alphanumeric information, 2-D images, graphs or other graphical images, either in separate areas of the display or in colored overlays.

Therefore, those skilled in the art will recognize that other embodiments could be practiced without departing from the scope and spirit of the claims set forth below.

What is claimed is:

1. An ultrasound imaging probe, comprising:
   a support element;
   a first imaging transducer array disposed on the support element;
   a second imaging transducer array disposed on the support element, wherein the first and second imaging transducer array image planes are non-parallel as a function of non-parallel positions of the first imaging transducer array relative to the second imaging transducer array; and
   a therapeutic tool attached adjacent to an imaging transducer array such that the therapeutic tool is substantially within a plane defined by one of the first and second imaging transducer arrays and respective first and second imaging transducer array image planes, wherein the therapeutic tool moves together with the first and second imaging transducer arrays.

2. The ultrasound imaging probe of claim 1, wherein the second imaging transducer array is spaced from the first imaging transducer array.

3. The ultrasound imaging probe of claim 1, wherein the second imaging transducer array is substantially orthogonal to the first imaging transducer array.

4. The ultrasound imaging probe of claim 1, further comprising a display guide representative of the current position of the therapeutic tool.

5. The ultrasound imaging probe of claim 1, further comprising a third imaging transducer array disposed on the support element, wherein the first and third imaging transducer array image planes are non-parallel.

6. The ultrasound imaging probe of claim 5, wherein the third imaging transducer array is spaced from the first imaging transducer array.

7. The ultrasound imaging probe of claim 5, wherein the third imaging transducer array is substantially orthogonal to the first imaging transducer array.

8. The ultrasound imaging probe of claim 1, wherein the therapeutic tool is a tissue-cutting or tissue-burning tool.

9. The ultrasound imaging probe of claim 1, wherein the therapeutic tool is an electrocautery device.

10. The ultrasound imaging probe of claim 1, further comprising a control wire connected with the therapeutic tool wherein the therapeutic tool is retractable.

11. The ultrasound imaging probe of claim 10, further comprising a finger hoop connected with the control wire wherein the therapeutic tool is retractable under the guidance of a user's fingers.

12. The ultrasound imaging probe of claim 1, wherein the therapeutic tool is a surgical blade.

13. The ultrasound imaging probe of claim 1, wherein the support element is semi-rigid and user-reformable.

14. An ultrasound imaging display method comprising generating a format comprising:
   display of a first image associated with a first image plane;
   display of a second image associated with a second image plane, wherein the first image plane and the second image plane are non-parallel and displayed simultaneously; and
   wherein at least one of the first or second images is distorted, producing a pseudo 3-D image.

15. The ultrasound imaging display format of claim 14, further comprising an icon, symbol, alphanumeric character, or graphical display representing a therapeutic tool.

16. The ultrasound imaging display format of claim 15 further comprising a display guide representative of the current position or deployment of the therapeutic tool.

17. The ultrasound imaging display format of claim 14, wherein the second image is distorted by a geometric transformation from an originally rectangular image into a trapezoidal image.

18. The ultrasound imaging display format of claim 14, wherein the first image plane is spaced from the second image plane.

19. The ultrasound imaging display format of claim 14, wherein the first image plane is substantially orthogonal to the second image plane.

20. The ultrasound imaging display format of claim 14 further comprising display of a third image in a third plane, spaced from the first image plane.

21. The ultrasound imaging display format of claim 20, wherein the third image plane and the first image plane are non-parallel.

22. The ultrasound imaging display format of claim 20, wherein the third image plane is substantially orthogonal to the first image plane.

23. The ultrasound imaging display format of claim 22, wherein the second and third image planes are substantially parallel.

24. The ultrasound imaging display format of claim 23, wherein both the second and third images are distorted to produce a pseudo 3-D image.

25. The ultrasound imaging display format of claim 24, further including an icon, symbol, alphanumeric character, or graphical display representing a therapeutic tool.

26. The ultrasound imaging display format of claim 25, wherein the therapeutic tool representation includes an indication of the position and/or state of operation of the tool.

27. The ultrasound imaging display format of claim 23, wherein the second and third images are distorted such that the second and third secondary imaging array data plane image lines are made to appear gradually shorter and hence further away.

28. The ultrasound imaging display format of claim 14, wherein the first and second image planes are angled in a symmetrical chevron and the first image is distorted substantially the same as the second image.

29. The ultrasound imaging display format of claim 14, wherein the second image is distorted such that the secondary imaging array data plane image lines are made to appear gradually shorter and hence further away.

30. A medical ultrasound imaging system comprising:
   an imaging probe including a support element;
   a first imaging transducer array disposed on the support element;
   a second imaging transducer array disposed on the support element, wherein the first imaging transducer array and the second imaging transducer array are non-parallel;
   a therapeutic tool attached to the support element, substantially adjacent to at least one of the imaging transducer arrays;
   a display for showing a displayed image resulting from imaging with the first and second imaging transducer arrays, wherein the imaging transducer arrays are maintained in a fixed relationship with respect to the moving therapeutic tool; and a display guide representative of the current position or deployment of the therapeutic tool.

31. The medical ultrasound imaging system of claim 30, wherein part of the displayed image comprises a geometric transformation of a 2-D image data set corresponding to the first imaging transducer array.

32. The medical ultrasound imaging system of claim 30, wherein the part of the displayed image comprises a trapezoidal image.

33. The medical ultrasound imaging system of claim 30, wherein the second imaging transducer array is spaced from the first imaging transducer array.

34. The medical ultrasound imaging system of claim 30, wherein the second imaging transducer array is substantially orthogonal to the first imaging transducer array.

35. The medical ultrasound imaging system of claim 30, further comprising a third imaging transducer array disposed on the support element, wherein the first imaging transducer array and the third imaging transducer array are non-parallel.

36. The medical ultrasound imaging system of claim 35, wherein the third imaging transducer array is spaced from the first imaging transducer array.

37. The medical ultrasound imaging system of claim 35, wherein the third imaging transducer array is substantially orthogonal to the first imaging transducer array.

38. The medical ultrasound imaging system of claim 30, wherein the therapeutic tool is a tissue-cutting or tissue-burning tool.

39. The medical ultrasound imaging system of claim 30, wherein the therapeutic tool is an electrocautery device.

40. The medical ultrasound imaging system of claim 30, wherein the therapeutic tool is retractable.

41. The medical ultrasound imaging system of claim 40, wherein the therapeutic tool is retractable under the guidance of a user's fingers.

42. The medical ultrasound imaging system of claim 30, wherein the therapeutic tool is a surgical blade.

43. The medical ultrasound imaging system of claim 30, wherein the support element is semi-rigid and user-reformable.

44. The medical ultrasound imaging system of claim 30, wherein the medical ultrasound imaging system is used in combination with an intra-vascular ultrasound catheter.

45. The medical ultrasound imaging system of claim 30, further comprising an ultrasound imaging probe, with a unique identification number assigned to the ultrasound imaging probe, readable by software to determine the number of times that the ultrasound imaging probe has been used.

46. The medical ultrasound imaging system of claim 30, further comprising an ultrasound imaging probe using a plano-concave type array.

47. The medical ultrasound imaging system of claim 30, further comprising an ultrasound imaging probe using a 1.5-D or 2-D type array.

48. The medical ultrasound imaging system of claim 30, further comprising permanent aperture limits incorporated at the array boundaries to eliminate array cross-talk interference.

49. A method for isolating a tissue structure, comprising the steps of:

observing the tissue structure with a plurality of imaging transducer arrays where at least two of the imaging transducer arrays are spaced apart;

moving a therapeutic tool together with the plurality of imaging transducer arrays; and activating the therapeutic tool under guidance of the plurality of imaging transducer arrays.

50. The method of claim 50, wherein the step of observing the tissue structure further comprises observing the tissue structure with a plurality of substantially orthogonal imaging transducer arrays.

51. The method of claim 49, wherein the step for moving a therapeutic tool further comprises moving a therapeutic tool under the guidance of a plurality of substantially orthogonal imaging transducer arrays.

52. The method of claim 49, wherein the step of activating the therapeutic tool further comprises activating the therapeutic tool under the guidance of a plurality of substantially orthogonal imaging transducer arrays.

53. The method of claim 49, wherein the therapeutic tool is a tissue-cutting or tissue-burning tool.

54. The method of claim 49, wherein the tissue structure is a blood vessel.

55. The method of claim 49, wherein the plurality of imaging transducer arrays is used in combination with an intra-vascular ultrasound catheter.

56. A method for an intra-operative procedure, comprising the steps of:

surgically forming a cavity;

inserting into the cavity a probe containing a plurality of imaging transducer arrays, and a retracted tissue cutting tool fixedly mounted with the probe adjacent the imaging transducer arrays;

observing tissue with the plurality of imaging transducer arrays;

moving the probe under guidance of the plurality of transducer arrays;

extending the tissue cutting tool from the probe; and retracting the tissue cutting tool from the extended position.

57. A method for switching between pseudo 3-D imaging of body tissue and 3-D imaging of body tissue with an multiple array imaging probe, comprising the steps of:

positioning a multiple array imaging probe near a body tissue;

selecting pseudo 3-D imaging of body tissue or 3-D imaging of the body tissue based on a voice command, foot pedal, keyboard, graphical user interface or an equivalent interface with an operator; and displaying pseudo 3-D images or 3-D images of the body tissue based on the selection of the operator.

58. A medical ultrasound imaging system, comprising:

a multiple array imaging probe, including a principal array used for imaging, and a secondary array which can selectively function as an imaging array to provide imaging data for pseudo 3-D imaging, or function as a tracking array to provide motion estimation data regarding the principal array for 3-D imaging;

selection means for an operator to select pseudo 3-D imaging or 3-D imaging; and a display to display pseudo 3-D images or 3-D images from data obtained from the principal array and the secondary array.

59. The method of claim 58 wherein the multiple array imaging probe includes a third transducer array which can selectively function as an imaging array for pseudo 3-D imaging, or function as a tracking array to provide motion estimation data regarding the principal array.

60. A method for determining the position of a foreign object in body tissue, comprising the steps of:

imaging the body tissue with an ultrasound imaging probe having a first transducer array and a second transducer array;

obtaining motion estimates regarding the first transducer array from the second transducer array of the ultrasound imaging probe to construct 3-D images of the body tissue and the foreign object; and displaying 3-D images or other information concerning the body tissue and foreign object from data obtained from the first and second transducer arrays.

61. The method of claim 60 wherein the ultrasound imaging probe is positioned in a surgically formed cavity.

62. The method of claim 60 wherein the foreign object is a surgical tool.

63. The method of claim 60 wherein the foreign object is a catheter.

64. The method of claim 60 wherein the foreign object is an IVUS catheter.

65. The method of claim 60 wherein the foreign object is a gallstone.

66. The method of claim 60 wherein the foreign object is a bullet, pellet, piece of shrapnel, or other projectile material.

67. The method of claim 60 wherein the steps of imaging the body tissue and obtaining motion estimates of the first transducer array include a third transducer array.

* * * * *